United States Patent [19]
Smith et al.

[11] Patent Number: 5,587,321
[45] Date of Patent: Dec. 24, 1996

[54] MOATED TISSUE CULTURE PLATE

[75] Inventors: Donald D. Smith, Blue Springs; Christopher B. Cohick, Kansas City, both of Mo.; Herbert B. Lindsley, Shawnee Mission, Kans.

[73] Assignee: University of Kansas, Lawrence, Kans.

[21] Appl. No.: 509,174

[22] Filed: Jul. 31, 1995

[51] Int. Cl.$^6$ .................................................. C12M 3/00
[52] U.S. Cl. ........................ 435/305.3; 435/305.4; 422/102
[58] Field of Search ............................. 422/101, 102; 435/288.4, 288.5, 305.1, 305.2, 305.3, 305.4

[56] References Cited

U.S. PATENT DOCUMENTS 3,791,930  2/1974  Saxholm .............................. 435/305.3

*Primary Examiner*—David A. Redding
*Attorney, Agent, or Firm*—Hovey, Williams, Timmons & Collins

[57] ABSTRACT

A culture plate apparatus having circular culture wells arranged in a cluster includes a moat surrounding the cluster with a cover for enclosing the wells and the moat with a head space therebetween. When the moat is filled with water or buffer solution, the moat maintains temperature uniformity among the wells and maintains uniform humidity in the head space thereby preventing nonuniform evaporation from the wells while reducing evaporation overall.

24 Claims, 1 Drawing Sheet

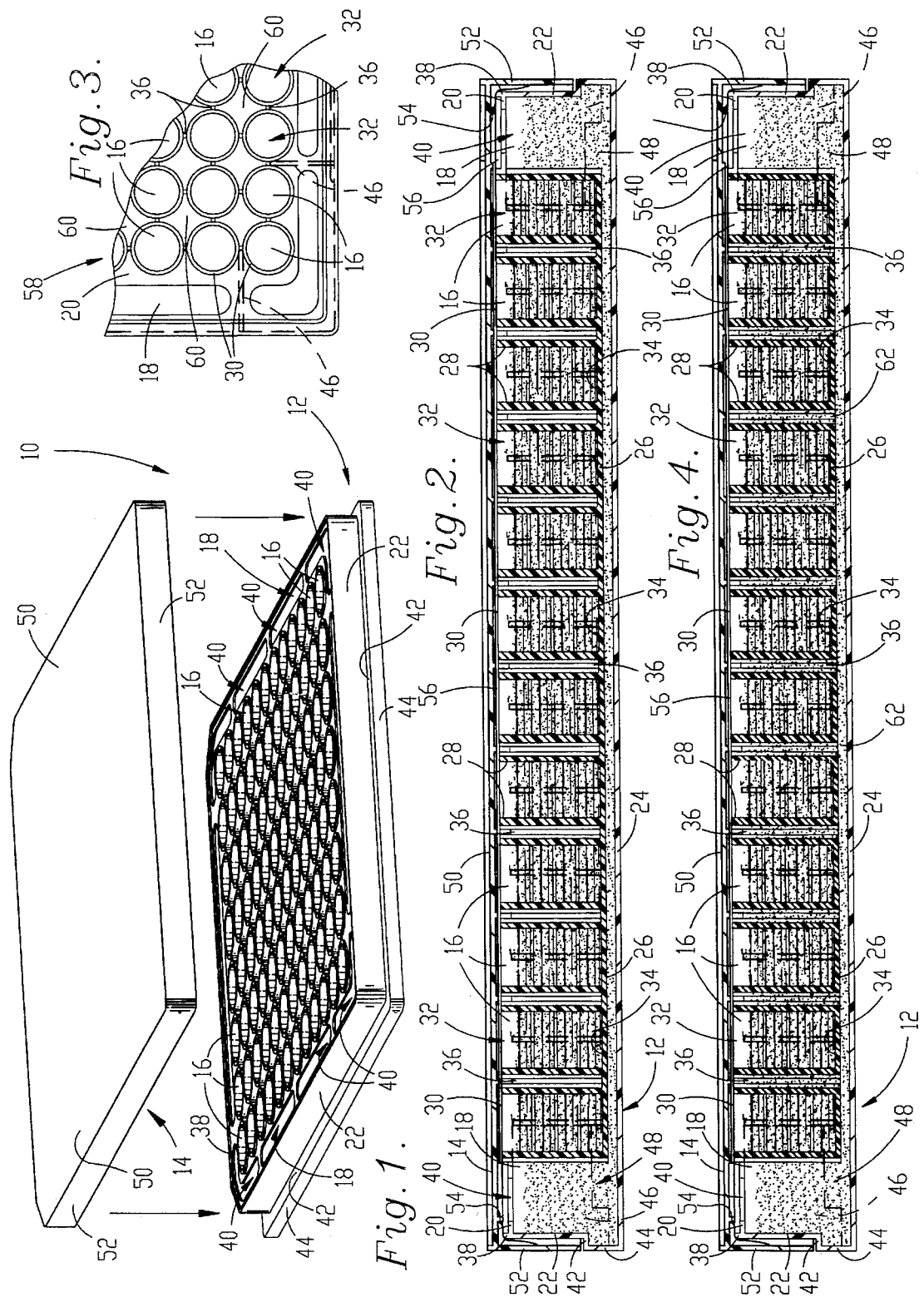

MOATED TISSUE CULTURE PLATE

BACKGROUND OF THE INVENTION

1. Field of the Invention

The present invention relates to the field of culture plates. More particularly, the invention is concerned with a culture plate apparatus including culture wells arranged in a cluster with a moat surrounding the cluster and including a cover for enclosing the wells and the moat with a head space therebetween. By filling the moat with water or buffer solution, the moat maintains temperature uniformity among the wells and maintains uniform humidity in the head space thereby preventing nonuniform evaporation from the wells while reducing evaporation overall.

2. Description of the Prior Art

In the prior art, tissue culture plates having a plurality of wells are used for biological culturing. A typical culture plate is known as tissue culture cluster dish and includes 96 wells arranged in a rectangular cluster of eight rows (designated A through H) of twelve wells (designated 1 through 12). A cover fits over the tray and encloses the tops of the wells. Similar cluster dishes are arranged in groups of six, twelve, twenty-four or forty-eight wells, respectively.

One of the problems with prior art culture trays is the evaporation of water from tissue culture medium placed in the wells. This problem is most noted over extended culturing periods and particularly acute for those wells around the periphery of the cluster.

A common way of coping with this evaporation problem is to fill the peripheral wells (36 in number) with water or buffer solution and use only the inner 60 wells for experimentation. The effect is a loss of over one third (36 of 96) of the available wells for experimentation which in turn requires the use of more trays and additional labor and time.

Another problem with prior art culture trays is sometimes temperature variations among the wells affects experimental results. Again, this problem is particularly acute with the wells around the periphery of the cluster.

SUMMARY OF THE INVENTION

The present invention solves the prior art problems discussed above and provides a distinct advance in the state of the art. More particularly, the culture tray apparatus hereof maintains uniformity of temperature and humidity among the wells, reduces evaporation overall, and allows effective use of all of the wells.

The preferred embodiment of the present invention includes a plurality of culture wells, a cover for enclosing the tops of the wells with a head space therebetween, and a liquid-receiving chamber in spanning relationship with at least two of the wells and having a chamber opening in communication with the head space. In preferred forms, the chamber surrounds the wells with a plurality of chamber openings with the head space. In one embodiment, the chamber includes the space beneath the wells. In another embodiment, the chamber includes the interstitial spaces between the wells. In other forms, the chamber is restricted to the moat surrounding the peripheral wells.

BRIEF DESCRIPTION OF THE DRAWING

FIG. 1 is a perspective view of the preferred culture tray apparatus configured in accordance with the present invention showing the cover positioned above the base;

FIG. 2 is a sectional view of the apparatus of FIG. 1 with the cover in place over the base;

FIG. 3 is a partial plan view of the base of the apparatus of FIG. 1; and

FIG. 4 is a sectional view of another embodiment of the apparatus of FIG. 1.

DETAILED DESCRIPTION OF THE PREFERRED EMBODIMENTS

Referring now the drawing figures, apparatus 10 includes base 12 and cover 14. Base 12 includes a plurality of tubular wells 16 and chamber 18 defined by top wall 20, side walls 22, base wall 24 and bottom well wall 26.

Wells 16 are arranged in a rectangular configuration of eight rows of twelve wells each. Each well 16 includes a tubular well wall 28 and presents well top 30 surrounding well opening 32 and presents well bottom 34. Gussets 36 interconnect adjacent tubular well walls 28. Bottom well wall 26 presents a rectangular configuration and functions as a common wall for enclosing well bottoms 34.

Top wall 20 surrounds the cluster of wells 16 and presents a marginal, upstanding closure ridge 38 for engaging cover 14. Top wall 20 further includes a plurality of chamber openings 40 defined therein preferably configured as slots.

Side walls 22 are configured to present surrounding shelf 42 with base extension 44 therebelow. A plurality of liquid-dampening baffles 46 couple the inner surfaces of side walls 22 with an opposite well gusset 36. It will be noted that there is a gap 48 between the bottom of each baffle 46 and base wall 24 for allowing liquid flow therethrough. Baffles 46 also serve to strengthen the overall structural integrity of base 12.

Cover 14 includes top panel 50 and downwardly extending, side panels 52. The lower face of top panel 50 includes guide ridge 54 spaced from side walls 52 and configured to receive closure ridge 38 in registration therebetween when cover 14 is placed on base 12. Cover side panels 52 are configured so that the outer faces thereof are flush with the outer face of base extension 44.

With cover 14 in place over base 12, cover 14 encloses well tops 30 and chamber openings 40. Furthermore, head space 56 is defined between the lower face of cover panel 50 and tops 30 and chamber openings 40. In this way, chamber 18 is in communication with head space 56 by way of chamber openings 40, and wells 16 are in communication with head space 56 by way of well openings 32.

In use, culture medium is placed in wells 16. Because of the present invention, all ninety-six of wells 16 can be used. A solution such as water, buffer or other liquid is then placed in chamber 18 by way of chamber openings 40. The solution flows through chamber 18 by way of gaps 48 around the periphery of the cluster of wells 16 and also under bottom well wall 26. Cover 14 is then placed over base 12. The solution may require the addition of a detergent to reduce surface tension and to allow the solution to flow into the interstitial spaces. Base wall 24 is removable in the preferred embodiment so that base 12 can be placed in a plate reader which performs reading through the bottoms of the wells.

The presence of the solution in chamber 18 provides excess solution vapor such as humidity into head space 56. This reduces the overall rate of evaporation of culture medium from wells 16 and further, ensures uniformity in the vapor above wells 16. Because of this, the outer wells along the periphery of the well cluster do not dry at a faster rate than any of the other wells and uniformity of culture evaporation is maintained. Moreover, the presence of the solution in chamber 18 ensures uniformity in the temperature of the cultures in wells 16. The solution itself, as a thermal mass, along with the presence of the solution about the periphery of the well cluster and beneath wells 16, ensures temperature uniformity among the wells 16.

FIG. 3 illustrates another embodiment 58 of the present invention which further enhances the benefits thereof. More particularly, embodiment 58 is the same as FIGS. 1–3 except that apertures 60 are defined in bottom well wall 26 at interstitial spaces 62. Accordingly, interstitial spaces 62 become part of chamber 18 and allow the solution therein to surround the well walls 28 as well as well bottoms 34.

Interstitial spaces 62 are open to head space 56 which provides additional solution surface area substantially surrounding each well 16. With the configuration of embodiment 58, the vapor uniformity in head space 56 is enhanced as is the thermal uniformity among wells 16. Furthermore, embodiment 58 provides increased solution mass available for evaporation and as a thermal sink.

As those skilled in the art will appreciate, the present invention encompasses many variations in the preferred embodiments described herein. For example, base wall 24 could be eliminated and bottom well wall extended to base side walls 22 in order to define chamber 18. Furthermore, ports could be defined from the periphery of the well cluster into interstitial spaces 62 in order to allow solution to flow through these ports to fill spaces 62. The present invention can also be used with different types of culture dishes including, for example, a microtiter plate used for biochemical and radiological assays. Having thus described the preferred embodiments of the preferred invention, the following is claimed as new and desired to be secured by Letters Patent:

We claim:

1. A culture plate apparatus comprising:
structure defining a plurality of culture wells presenting respective top openings;
a frame supporting said wells; and
a cover configured for enclosing said top openings with a head space therebetween,
said frame including means defining a liquid-receiving chamber in spanning relationship with at least two of said wells, said frame having a chamber opening in communication with said head space, said frame being permanently secured to said structure defining said plurality of culture wells.

2. The apparatus as set forth in claim 1, said wells being arranged in a cluster presenting a periphery, said chamber extending along said periphery.

3. The apparatus as set forth in claim 2, said chamber surrounding said cluster.

4. The apparatus as set forth in claim 3, said frame including means defining a plurality of said chamber openings.

5. The apparatus as set forth in claim 3, said wells presenting respective well bottoms, said frame including a base wall positioned below said well bottoms with an open area therebetween, said chamber including said open area.

6. The apparatus as set forth in claim 3, said wells presenting interstitial spaces therebetween, said chamber including said interstitial spaces.

7. The apparatus as set forth in claim 3, said frame including a plurality of baffles positioned in said chamber.

8. The apparatus as set forth in claim 5, said base wall being removable.

9. The apparatus as set forth in claim 1, said wells presenting a circular configuration in cross section.

10. The apparatus as set forth in claim 1, said wells being arranged in a rectangular cluster.

11. The apparatus as set forth in claim 10, said cluster including eight rows of twelve wells.

12. A culture plate apparatus comprising:
structure defining a plurality of culture wells presenting respective well tops and arranged in a cluster presenting a periphery;
a frame supporting said wells; and
a cover configured for enclosing said well tops with a head space therebetween,
said frame including a continuous, upstanding sidewall disposed about said cluster and in spaced relationship to said cluster periphery, said sidewall presenting an inner face adjacent said cluster periphery and an opposed outer face, said frame defining a liquid-receiving chamber between said sidewall inner face and said cluster periphery, said frame including a laterally extending top wall between said sidewall and cluster periphery, said chamber being located beneath said top wall and between said sidewall inner face and said cluster periphery, said top wall being apertured with chamber openings for communicating said chamber and said head space, said cover being configured for enclosing said chamber openings with said head space therebetween.

13. The apparatus as set forth in claim 12, said wells presenting respective well bottoms, said frame including a base wall positioned below said well bottoms with an open area therebetween, said chamber including said open area.

14. The apparatus as set forth in claim 13, said wells presenting interstitial spaces therebetween, said chamber including said interstitial spaces.

15. The apparatus as set forth in claim 12, said frame including a plurality of baffles positioned in said chamber.

16. The apparatus as set forth in claim 12, said wells presenting a circular configuration in cross section.

17. The apparatus as set forth in claim 12, said wells being arranged in a rectangular cluster.

18. The apparatus as set forth in claim 17, said cluster including eight rows of twelve wells.

19. A culture plate apparatus comprising:
structure defining a plurality of culture wells presenting respective top openings;
a frame supporting said wells; and
a cover configured for enclosing said top openings with a head space therebetween,
said frame including means defining a liquid-receiving chamber in spanning relationship with at least two of said wells, said frame having a chamber opening in communication with said head space, said wells being arranged in a cluster presenting a periphery, said chamber extending along said periphery, said chamber surrounding said cluster, said wells presenting respective well bottoms, said frame including a base wall positioned below said well bottoms with an open area therebetween, said chamber including said open area.

20. The apparatus as set forth in claim 19, said base wall being removable.

21. A culture plate apparatus comprising:
structure defining a plurality of culture wells presenting respective top openings;
a frame supporting said wells; and a cover configured for enclosing said top openings with a head space therebetween, said frame including means defining a liquid-receiving chamber in spanning relationship with at least two of said wells, said frame having a chamber opening in communication with said head space, said frame including a plurality of baffles positioned in said chamber, said wells being arranged in a cluster presenting a periphery, said chamber extending along said periphery, said chamber surrounding said cluster.

22. A culture plate apparatus comprising:

structure defining a plurality of culture wells arranged in a cluster presenting a periphery, each of said wells including a top opening, a bottom wall, and an upstanding tubular sidewall permanently secured to said bottom wall to define a liquid-impervious concavity;

a frame for supporting said cluster, said frame including a continuous, upstanding sidewall disposed about said cluster and in spaced relationship to said cluster periphery, said sidewall presenting an inner face adjacent said cluster periphery and an opposed outer face, said frame defining a chamber between said sidewall inner face and said cluster periphery for receiving a humidifying liquid; and a cover including a top plate and a continuous, depending flange for placement over said cluster and said chamber with said flange adjacent said sidewall outer face, said cover being configured to define a head space between said cover and said top openings of said wells, said chamber being in communication with said head space for facilitating even humidification of said wells.

23. The apparatus as set forth in claim 22, said frame including a laterally extending top wall between said sidewall and cluster periphery and beneath said top openings of said wells, said chamber being located beneath said top wall and between said sidewall inner face and said cluster periphery, said top wall being apertured for communicating said chamber and said head space.

24. The apparatus as set forth in claim 22, said frame defining open regions between said wells and inboard of said cluster periphery for permitting entrance of said humidifying liquid between said wells.

* * * * *